(12) United States Patent
Harrington et al.

(10) Patent No.: US 7,632,940 B2
(45) Date of Patent: Dec. 15, 2009

(54) PROCESS FOR THE PREPARATION OF 4'-AZIDO CYTIDINE DERIVATIVES

(75) Inventors: Peter John Harrington, Louisville, CO (US); Stefan Hildbrand, Moehlin (CH); Keshab Sarma, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 186 days.

(21) Appl. No.: 11/999,926

(22) Filed: Dec. 7, 2007

(65) Prior Publication Data

US 2008/0161550 A1  Jul. 3, 2008

(30) Foreign Application Priority Data

Dec. 11, 2006 (EP) .................................. 06125768

(51) Int. Cl.
*C07H 21/00* (2006.01)
(52) U.S. Cl. .................. 536/25.3; 536/22.1; 536/25.31; 536/28.1; 536/28.4; 536/28.5
(58) Field of Classification Search ........................ None
See application file for complete search history.

(56) References Cited

FOREIGN PATENT DOCUMENTS

| WO | WO 2004/046159 A1 | 6/2004 |
|---|---|---|
| WO | WO 2005/000864 A1 | 1/2005 |

*Primary Examiner*—Patrick T Lewis
(74) *Attorney, Agent, or Firm*—Brian L. Buckwalter

(57) ABSTRACT

The invention relates to a novel process for the preparation of 4'-azido-cytidine (I) or a

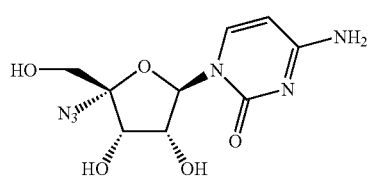

pharmaceutically accepted salt thereof. The compound of formula I is useful for treating virus mediated diseases, particularly for treating HCV mediated diseases.

14 Claims, No Drawings

PROCESS FOR THE PREPARATION OF 4'-AZIDO CYTIDINE DERIVATIVES

CROSS REFERENCE TO RELATED APPLICATIONS

This application claims priority under 35 USC §119 from European Application EP06125768.9 filed Dec. 11, 2006 and which are incorporated herein by reference in full.

FIELD OF THE INVENTION

The invention relates to a novel process for the preparation of a 4'-azido cytidine (I)

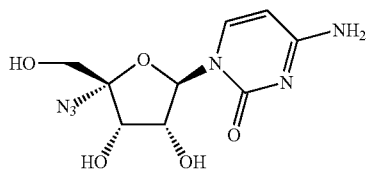

or of a pharmaceutically accepted salt thereof. The compound of formula I is useful for treating virus mediated diseases, particularly for treating HCV mediated diseases. The present invention relates to improvements in the process useful for the manufacture of compounds of formula I.

BACKGROUND OF THE INVENTION

The 4'-azido cytidine of formula I has been disclosed by Maag et al. (*J. Med. Chem.* 1992 35:1440) and by R. R. Devos et al (WO 02/100415). Synthetic pathways for its preparation have been described in the PCT Publication WO 2004/046159 A1 and WO 2005/000864 A1.

For the transformation of the intermediate 4'-azido-triacyl uridine into the desired 4'-azido-cytidine it was suggested to run the reaction in the presence of triazole, phosphorous oxychloride and triethylamine. However it was found that the use of triazole is not favorable on a technical scale process due to its low biodegradability. The object of the present invention therefore was to provide a process which can be performed on a technical scale and which is not suffering from the disadvantages as outlined above.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used herein, unless specifically indicated otherwise, the word "or" is used in the "inclusive" sense of "and/or" and not the "exclusive" sense of "either/or".

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-⇌-C(—OH)=CH—) amide/imidic acid (—C(=O)—NH-⇌-C(—OH)=N—) and amidine (—C(=NR)—NH-⇌-C(—NHR)=N—) tautomers. The latter two are particularly common in heteroaryl and heterocyclic rings and the present invention encompasses all tautomeric forms of the compounds.

The process of the present invention comprises the a process to prepare 4'-azido-

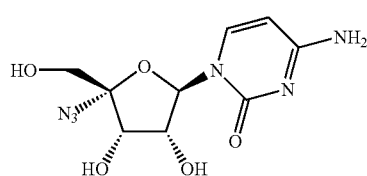

cytidine (I) or of a pharmaceutically accepted salt thereof, which process is characterized by:

a) a protected 4'-azido-nucleoside of the formula II wherein:

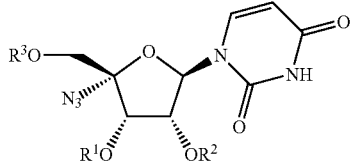

R$^1$ and R$^2$ are independently selected from COR$^4$ and C(=O)OR$^4$ or R$^1$ and R$^2$ together form a —CH$_2$—, —C(CH$_3$)$_2$—, —CH-phenyl-, or —CH(OMe)— bridge;

R$^3$ is selected from COR$^4$ and C(=O)OR$^4$ and

R$^4$ is independently C$_{1-12}$-alkyl, phenyl optionally substituted with 1 to 3 substituents selected from the group consisting of C$_{1-6}$-alkyl, C$_{1-6}$-alkoxy, halogen, nitro or cyano is reacted with imidazole, phosphorous oxychloride and triethylamine to form the imidazole compound of formula IIIa wherein R$^1$, R$^2$ and R$^3$ are as above;

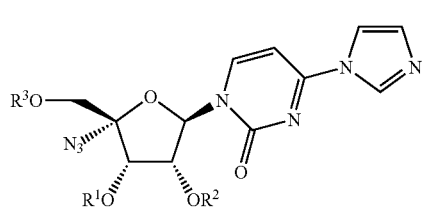

b) the imidazole compound of formula IIIa is subjected to ammonolysis with aqueous ammonia to form the amine of formula of formula IIIb wherein R$^1$, R$^2$ and R$^3$ are as above, and

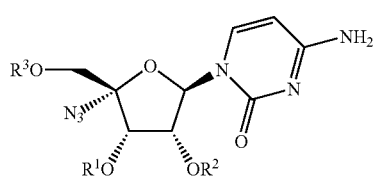

c) the amine of formula IIIb is finally transformed into the 4'-azido-cytidine of formula I.

Step a comprises the transformation of a protected 4'-azido-uridine derivative of

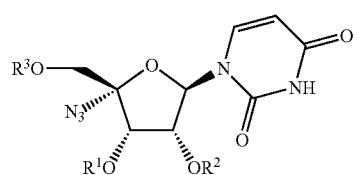

formula II wherein R$^1$, R$^2$ and R$^3$ are as above with imidazole, phosphorous oxychloride and triethylamine into the imidazole compound of formula IIIa wherein

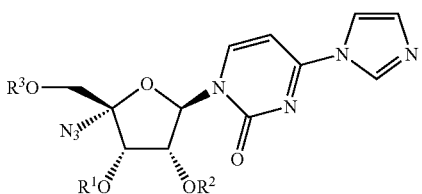

R$^1$, R$^2$ and R$^3$ are as above. The 4'-azido-nucleosides of formula II can be synthesized e.g. following the procedure disclosed in examples 1 to 5 of the PCT Publication WO 2005/000864 A1.

Usually the process is performed in the presence of a first organic solvent, preferably in methylene chloride, THF or 2-methyltetrahydrofuran at a reaction temperature of 0° C. to 80° C., preferably of 20° C. to 65° C.

The imidazole generally is present in an excess which is from 4.0 equivalents to 10.0 equivalents, preferably from 5.0 equivalents to 8.0 equivalents related to one equivalent of the 4'-azido-triacyl nucleoside of formula II.

The reaction is run in the presence of 1.0 equivalent to 2.0 equivalents, preferably from 1.4 equivalents to 1.7 equivalents with phosphorous oxychloride related to one equivalent of the 4'-azido-triacyl nucleoside of formula II.

The imidazole compound of formula IIIa is a novel compound and therefore is a further embodiment of the present invention.

Particularly preferred is the imidazole compound of formula IIIa wherein R$^1$ and R$^2$ are benzoyl or R$^1$ and R$^2$ together form a —CH(OMe)— bridge and R$^3$ is 3-chlorbenzoyl.

The imidazole compound of formula IIIa can be isolated from the reaction mixture following procedures known to those skilled in the art for instance by recovering it from the organic phase e.g. by evaporation. As a rule the imidazole compound of formula IIIa is directly, without isolating it from the organic phase, subjected to the ammonolysis in step b.

Step b comprises ammonolysis of the imidazole compound of formula IIIa with aqueous ammonia to form the amine of formula IIIb.

The ammonolysis is commonly performed in a second organic solvent such as methylene chloride, tetrahydrofuran or 2-methyltetrahydrofuran, preferably tetrahydrofuran or 2-methyltetrahydrofuran at a temperature of 20° C. to 60° C., preferably of 25° C. to 45° C.

Suitable aqueous ammonia solutions have an ammonia content of 20% to 30%, as a rule of about 25%.

The duration of the ammonolysis largely depends on the amount of ammonia and the reaction temperature. One skilled in the art can monitor the reaction and determine the optimal duration for the reaction.

The amine of formula IIIb can be isolated following methods known to the skilled in the art, but is as a rule directly used in step c.

Step c comprises the deprotecting the amine of formula IIIb to afford 4'-azido-cytidine (I).

In case R$^1$, R$^2$ and R$^3$ are independently selected from COR$^4$ and C(=O)OR$^4$ the transformation in step c) is a methanolysis performed in aqueous ammonia and methanol at a temperature of 20° C. to 60° C.

Methanol can be introduced by distilling off the solvent used in step b) from the reaction mixture and by replacing it by methanol.

Methanolysis then can be effected by the addition of aqueous ammonia solution and by performing the reaction at a temperature of 20° C. to 60° C., preferably of 25° C. to 45° C. Suitable aqueous ammonia solutions were similar to those in the description of step b) above.

In case $R^1$ and $R^2$ taken together form a —$CH_2$—, —$C(CH_3)_2$—, —CH-phenyl- or —CH(OMe)— bridge and $R^3$ is independently selected from $COR^4$ and $C(=O)OR^4$ wherein $R^4$ is as defined above, the deprotection in step c) comprises a first methanolysis step performed in aqueous ammonia and methanol at a temperature of 20° C. to 60° C. to cleave the acyl group $R^3$ and a second acidic treatment to cleave the bridge formed by $R^1$ and $R^2$.

The methanolysis can be performed as described above.

For the acidic treatment a mineral acid like hydrochloric acid or sulfuric acid or a short chain carboxylic acid such as formic acid or acetic acid may be used. The cyclic acetal formed by $R^1$ and $R^2$ is preferably cleaved with formic acid at room temperature.

The isolation of the desired 4'-azido cytidine of formula I can take place applying methods known to the skilled in the art for instance by exchanging the solvent from methanol to e.g. acetone/ethylacetate and by filtering off the precipitated product.

In a further embodiment of the invention the process of the present invention as described above can be used for the preparation of the tri-isobutyryloxy compound of formula IV.

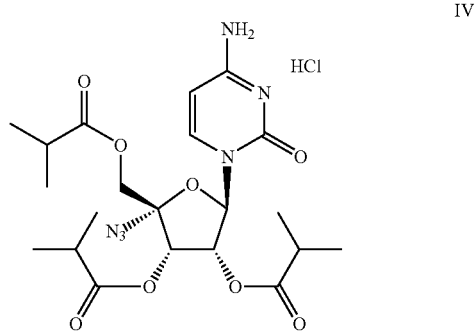

IV

This can be achieved by transforming the 4'-azido-cytidine of formula I with isobutyryl chloride in the presence of 4-(dimethylamino)-pyridine and triethylamine in a mixture of water and an organic solvent. Suitable organic solvent is tetrahydrofuran. The reaction temperature is usually selected in the range of −5° C. to 30° C. Isolation of the tri-isobutyryloxy compound of formula IV can happen by an aqueous work-up, followed by a solvent exchange to isopropanol/heptane and acidifying with hydrochloric acid. Conditions for acylation of cytidine compounds have been disclosed by K. Sarma in WO2007039413 published Apr. 12, 2007.

The term "$C_{1-12}$— alkyl" as used herein denotes an unbranched or branched chain hydrocarbon residue containing 1 to 12 carbon atoms. Representative $C_{1-12}$—alkyl groups include methyl, ethyl, propyl, i-propyl, n-butyl, i-butyl, t-butyl, pentyl or hexyl, heptyl, octyl, nonyl, decyl, undecyl or dodecyl.

The term "$C_{1-6}$— alkoxy" as used herein denotes an unbranched or branched chain $C_{1-6}$-alkyl oxy residue containing 1 to 6 carbon atoms. Representative $C_{1-6}$— alkoxy groups include methyoxy, ethoxy, propyloxy, i-propyloxy, n-butyloxy, i-butyloxy, t-butyloxy, pentyloxy or hexyloxy.

The term "halogen" as used herein refers to fluoro, chloro, bromo and iodo, preferably to chloro.

The term pharmaceutically acceptable salts as used herein refers to salts of the 4'-azido-cytidine of formula I with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

A "protective group" or "protecting group" means a group temporarily incorporated into a molecule which selectively blocks one reactive site in a multifunctional compound such that a chemical reaction can be carried out selectively at another unprotected reactive site in the meaning conventionally associated with it in synthetic chemistry. The term "deprotection" refers to the process of removing a protecting group.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The following examples shall illustrate the process of the present invention without limiting it.

EXAMPLES

Abbreviations

Bz=Benzoyl; (Cl) Bz=m-chlorobenzoyl; MeTHF=2-Methyltetrahydrofuran; DMAP=4-(dimethylamino)-pyridine; THF=Tetrahydrofuran Example 1

Preparation of 4-amino-1-((2R, 3R, 4S, 5R)-5-azido-3,4-dihydroxy-5-hydroxymethyl-tetrahydro-furan-2-yl)-1H-pyrimidin-2-one

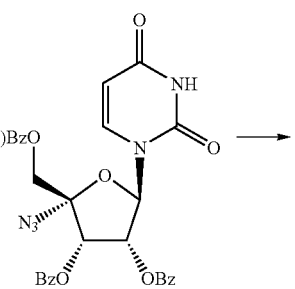

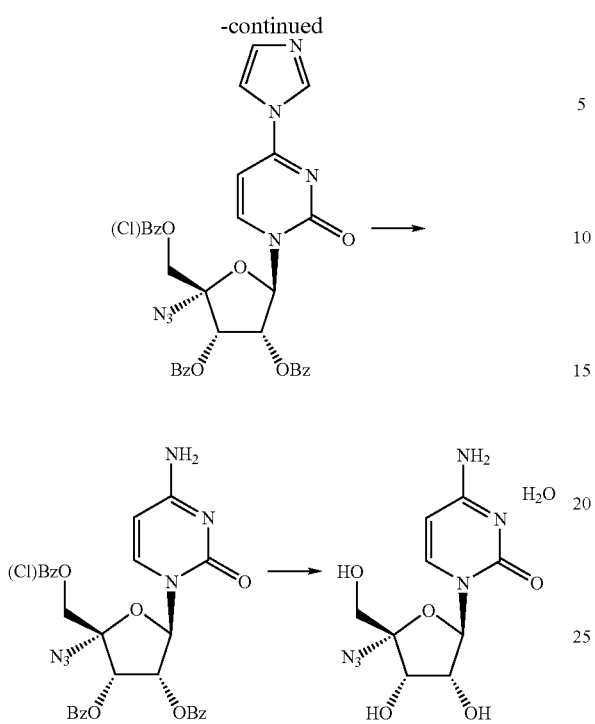

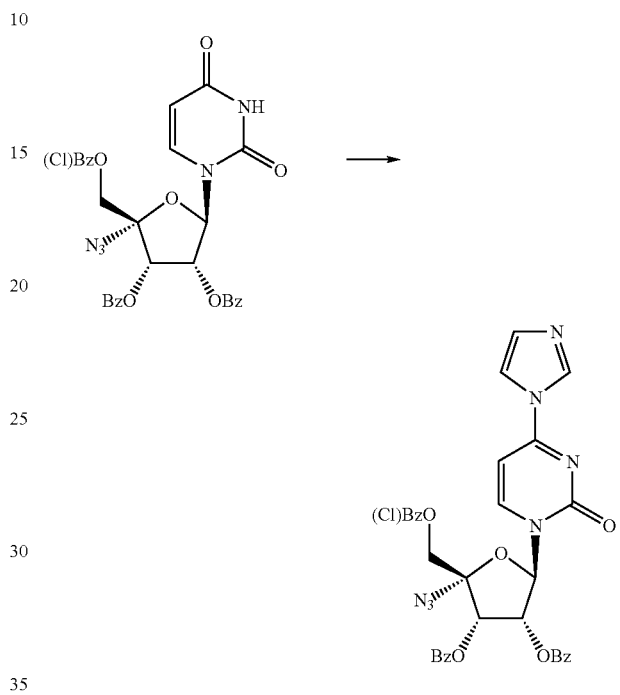

Example 2

Preparation of 3-chlorobenzoic acid (2R, 3S, 4R, 5R)-2-azido-3,4-bis-benzoyloxy-5-(4-imidazol-1-yl-2-oxo-2H-pyrimidin-1-yl)-tetrahydro-furan-2-ylmethyl ester A suspension of 100 g (0.158 mol) 3-chlorobenzoic acid (2R,3S,4R,5R)-2-azido-3,4-bis-benzoyloxy-5-(2,4-dioxo-3,4-dihydro-2H-pyrimidin-1-yl)-tetrahydro-furan-2-ylmethyl ester and 86.6 g (1.266 mol) imidazole in 500 ml MeTHF was treated at room temperature with 64 g (0.632 mol) triethylamine. The resulting mixture was treated at 20 to 45° C. within 30 to 120 minutes with 36.8 g (0.238 mol) phosphorous oxychloride. After the addition the mixture was heated to 55 to 65° C. and stirred at this temperature for 5 to 6 hours. The mixture was then cooled to 15 to 25° C. and treated at this temperature with 300 ml water. The layers were separated and the aqueous layer was extracted with MeTHF (1×50 ml). The combined organic layer was treated at 20 to 30° C. within 10 to 20 minutes with 54 g ammonia (25% solution in water). The mixture was heated to 40° C. and stirred at this temperature for 7 to 9 hours. After complete conversion the lower aqueous layer was separated and from the organic layer MeTHF was distilled off and replaced by methanol. The methanolic solution (approximately 400 ml) was then treated at 30 to 40° C. with 108 g ammonia (25% solution in water) and the resulting mixture was stirred for 5 hours at 35 to 40° C. Methanol was then distilled off and continuously replaced by 400 ml acetone, whereby the product precipitated. To complete precipitation 500 ml ethyl acetate was added at room temperature. The resulting suspension was cooled to 0 to 5° C. within 2 to 4 hours and stirred at this temperature for additional 2 hours. The crystals were filtered, washed in two portions with a pre-cooled mixture of 124 ml ethyl acetate and 62 ml acetone and dried in vacuo (<30 mbar) at 45° C. for 5 hours to afford 43.3 g (90.5%) of 4-amino-1-((2R,3S,4S,5R)-5-azido-3,4,-hydroxy-5-hydroxymethyl-tetrahydro-furan-2-yl)-1H-pyrimidin-2-one as the monohydrate with an assay of 99.4% (m/m).

A suspension of 30.0 g (47.5 mmol) 3-chlorobenzoic acid (2R,3S,4R,5R)-2-azido-3,4-bis-benzoyloxy-5-(2,4-dioxo-3,4-dihydro-2H-pyrimidin-1-yl)-tetrahydro-furan-2-ylmethyl ester and 26.0 g (380 mmol) imidazole in 110 ml MeTHF was treated at room temperature with 19.2 g (189 mmol) triethylamine. The resulting mixture was treated at 10 to 20° C. within 30 minutes with 11.03 g (71.2 mmol) phosphorous oxychloride. The mixture was heated to 60° C. and stirred at this temperature for 5 hours. The mixture was then cooled to 15° C. and treated at this temperature with 125 ml water. The layers were separated and the aqueous layer was extracted with MeTHF (1×30 ml). From the organic layer MeTHF was completely removed by distillation and replaced by 250 ml acetonitrile. Water (50 ml) and methylene chloride (100 ml) were added and the layers were separated. The aqueous layer was extracted with methylene chloride (1×100 ml). The organic layer was filtered, the solvent was evaporated and the residue (34.2 g) dried in vacuo (<30 mbar) at 40° C. for 16 hours to afford 29.7 g (90.8%) of 3-chlorobenzoic acid (2R, 3S,4R,5R)-2-azido-3,4-bis-benzoyloxy-5-(4-imidazol-1-yl-2-oxo-2H-pyrimidin-1-yl)-tetrahydro-furan-2-ylmethyl ester with an assay of 99.3% (area).

$^1$H NMR (CDCl$_3$) δ4.87 (s, 2H); 6.04-6.07 (m, 2H); 6.33 (dd, 1H); 6.51 (d, 1H); 7.20-7.41 (m, 6H); 7.49-7.60 (m, 3H); 7.69 (s, 1H); 7.89-8.06 (m, 7H); 8.37 (s, 1H).

IR: 2923, 2854, 2120 (—N$_3$), 1730, 1678, 1633, 1545, 1469, 1247, 1127, 929, 709, 476 cm$^{-1}$.

MS: 682 (M$^+$+1).

Example 3

Preparation of 4-amino-1-((3aR, 4R, 6aS, 6R)-6-azido-6-hydroxymethyl-2-methoxy-tetrahydrofuro[3,4-d]1,3-dioxol-4-yl)-1H-pyrimidin-2-one.

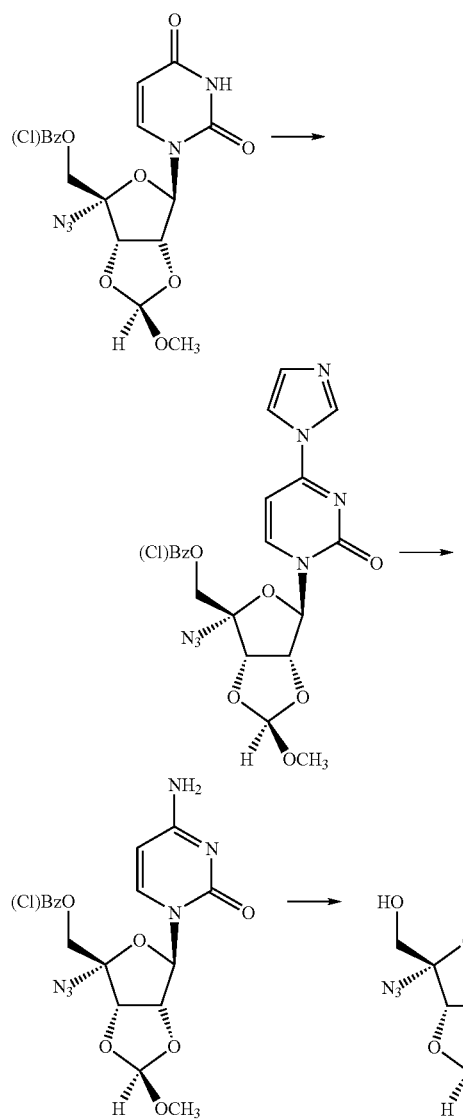

To a suspension of 0.69 g (10.11 mmol) imidazole and 1.07 g (10.5 mmol) triethylamine in 9 ml methylene chloride was added dropwise at −5 to 0° C. within 15 minutes 0.49 g (3.22 mmol) phosphorous oxychloride. After 15 minutes at −5° C., the resulting suspension was treated with 1.00 g (2.15 mmol) 3-chloro-benzoic acid 4-azido-6-(2,4-dioxo-3,4-dihydro-2H-pyrimidin-1-yl)-2-methyl-tetrahydro-furo[3,4-d]-1,3-dioxol-4-ylmethyl ester followed by 1 ml methylene chloride. The suspension was allowed to warm to room temperature within 15 minutes and then stirred at room temperature for 69 hours. The suspension was cooled to 0° C. and treated at this temperature with 10 ml water. The suspension was allowed to warm to room temperature and the layers were separated. The aqueous layer was extracted with methylene chloride (2×5 ml). The combined organic layer was dried over MgSO$_4$, filtered, concentrated in vacuo, and dried in vacuo (<10 mbar) at 25° C. for 22 hours to afford 1.07 g (96%) of 3-chlorobenzoic acid 4-azido-6-(4-imidazol-1-yl-2-oxo-2H-pyrimidin-1-yl)-2-methyl-tetrahydro-furo[3,4-d]-1,3-dioxol-4-ylmethyl ester as a beige foam.

$^1$H NMR (500 MHz, CDCl$_3$) δ 3.36 (s, 3H); 4.71 (d, J=12.5 Hz, 1H); 4.77 (d, J=11.5 Hz, 1H); 5.04 (d, J=5.5 Hz, 1H); 5.44 (dd, J=5.5 Hz, J=1.5 Hz, 1H); 6.03 (m, 2H); 6.55 (d, J=7.0 Hz, 1H); 7.21 (dd, J=1.5 Hz, J=0.5 Hz, 1H); 7.42 (dd, J=7.5 Hz, J=7.5 Hz, 1H); 7.58 (m, 1H), 7.70 (dd, J=2.0 Hz, J=2.0 Hz, 1H), 7.96 (m, 1H); 8.02 (d, J=8.0 Hz, 1H); 8.04 (dd, J=2.0 Hz, J=2.0 Hz, 1H); 8.40 (dd, J=1.0 Hz, J=1.0 Hz, 1H).

1.055 g (2.05 mmol) of this foam was dissolved in 10 ml THF and treated with 0.90 g ammonia (28% solution in water). The resulting solution was stirred at 25° C. for 24 hours. The solution was then concentrated on a rotary evaporator at 25° C. and 70 to 30 mm Hg. Methanol (10 ml) was added followed by 0.90 g ammonia (28% solution in water) and the resulting solution was stirred at 25° C. for 22 hours. The solution was concentrated on a rotary evaporator and the residue purified by radial chromatography on silica gel using first ethyl acetate followed by ethyl acetate/methanol 5:1 as eluent to afford 0.68 g (102%) of 4-amino-1-((2S,4R,3aS,6aS,6R)-6-azido-6-hydroxymethyl-2-methyl-tetrahydrofuro[3,4-d]-1,3-dioxol-4-yl)-1H-pyrimidin-2-one as a beige solid.

Example 4

Preparation of dodecanoic acid (2R, 3S, 4R, 5R)-5-(4-amino-2-oxo-2H-pyrimidin-1-yl)-2-azido-3,4-dihydroxy-tetrahydro-furan-2-ylmethyl ester

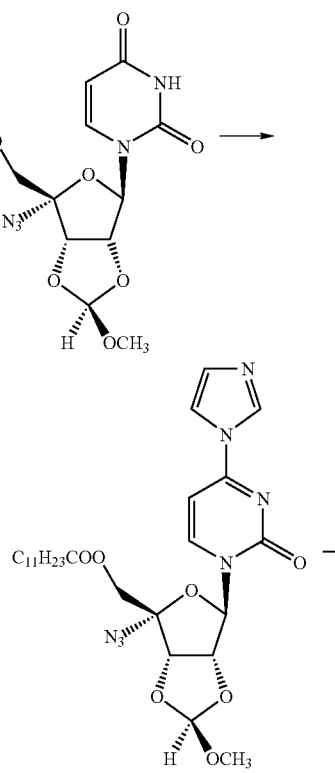

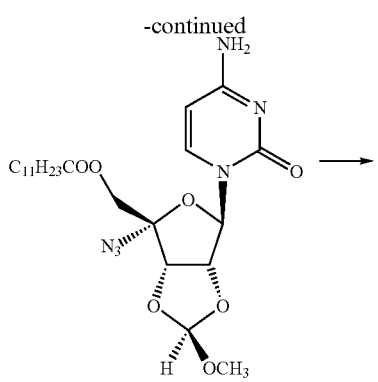

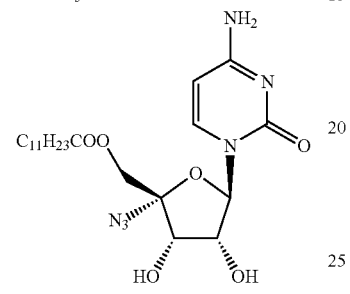

A solution of 1.35 g (8.83 mmol) phosphorus oxychloride in 5 ml methylene chloride was added dropwise at 0 to −5° C. within 15 minutes to a suspension of 1.89 g (27.7 mmol) imidazole and 2.92 g (28.9 mmol) triethylamine in 20 ml methylene chloride and the resulting suspension was stirred at −5° C. for 15 minutes. A solution of the azidoester (3.00 g, 5.89 mmol) in 12 ml methylene chloride was added and the resulting suspension was allowed to warm from 0 to 25° C. within 10 minutes and then stirred at 25° C. for 69 hours. The suspension was cooled to 0° C. and 30 ml of water was added dropwise at 0 to 5° C. The suspension was allowed to warm to 20° C. and the layers were separated. The aqueous layer was extracted with methylene chloride (2×5 ml). The combined organic layers were dried (MgSO$_4$), filtered, concentrated in vacuo, and dried in vacuo (10 mbar) at 25° C. for 5 hours to afford 3.13 g (95.0%) of the imidazole derivative as a beige foam. This foam was dissolved in 30 ml dry THF and the resulting solution was treated with 2.49 g (19.9 mmol) ammonia (28% solution in water). After 23 hours at 25° C. the solution was concentrated in vacuo, and dried in vacuo (<10 mbar) at 25° C. for 10 hours to afford 3.30 g of a pale yellow solid. This solid was recrystallized from hot methanol (50° C.) to afford 1.27 g of the methoxymethylene protected cytidine derivative as a colorless solid.

1.20 g (2.36 mmol) of this solid was treated with 4.8 ml formic acid (96%) and the resulting suspension was stirred at 25° C. for 4 hours. Water (4.8 ml) was then added followed by 10.5 ml ammonia (28% solution in water) to adjust the pH to pH 9. After one hour at 25° C. the precipitate was filtered, washed with 10 ml water, and dried in vacuo (<10 mbar) at 25° C. for 16 hours to afford 1.10 g (40%) of dodecanoic acid (2R,3R,4S,5R)-5-(4-amino-2-oxo-2H-pyrimidin-1-yl)-2-azido-3,4-dihydroxy-tetrahydro-furan-2-ylmethyl ester as a colorless solid. An analytical sample was obtained by recrystallization from hot methanol.

$^1$H NMR (500 MHz, DMSO-d$_6$) δ0.85 (t, J=7.0 Hz, 3H); 1.18-1.30 (m, 16H); 1.53 (m, 2H); 2.33 (t, J=7.5 Hz, 2H); 3.78 (t, J=5.0 Hz, 1H); 4.29 (d, J=12.0 Hz, 1H); 4.41 (d, J=12.0 Hz, 1H); 4.53-4.57 (m, 1H); 5.60 (br, 1H); 5.83 (d, J=8.0 Hz, 1H); 5.98 (br, 1H); 6.17 (d, J=8.0 Hz, 1H), 7.33 (br, 2H), 7.65 (d, J=7.0 Hz, 1H)

$^{13}$C NMR (125 MHz, DMSO-d$_6$) δ 173.0, 166.2, 156.2, 142.0, 97.9, 96.3, 89.6, 74.7, 72.1, 65.1, 34.0, 32.0, 29.7, 29.5, 29.4, 29.3, 29.0, 25.0, 22.8, 14.7.

IR (KBr): 3538, 3400, 3288, 2924, 2850, 2116, 1759, 1672, 1641, 1593, 1523 cm$^{-1}$.

Example 5

Preparation of isobutyric acid (2R, 3S, 4R, 5R)-5-(4-amino-2-oxo-2H-pyrimidin-1-yl)-2-azido-3,4-bis-isobutyryloxy-tetrahydro-furan-2-ylmethyl ester Hydrochloride

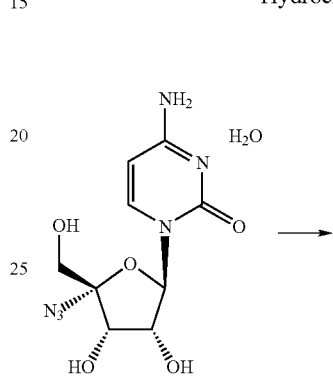

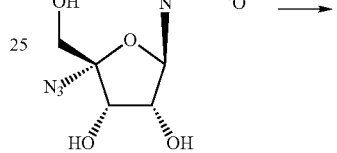

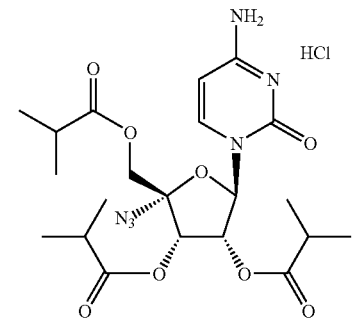

A suspension of 21.6 g (0.070 mol) 4-amino-1-((2R,3S,4S,5R)-5-azido-3,4,-hydroxy-5-hydroxymethyl-tetrahydro-furan-2-yl)-1H-pyrimidin-2-one and 88 mg (0.72 mmol) DMAP in 102 ml THF and 40 ml water was treated at −5 to 0° C. with 35.8 g (0.354 mol) triethylamine. The mixture was then treated at −5 to 20° C. within 1 to 2 hours with 29.5 g (0.271 mol) isobutyryl chloride and the resulting mixture was allowed to warm to room temperature and stirred at room temperature for one hour. After complete conversion 110 ml ethyl acetate followed by 30 ml water were added and the pH was adjusted to pH 6.5 to 7.0 by the addition of approximately 6.8 g hydrochloric acid (37% in water). The layers were allowed to separate, the lower aqueous layer was removed and the organic layer was washed with water (1×50 ml). From the organic layer ethyl acetate and THF were distilled off and completely replaced by isopropanol. The isopropanolic solution (approximately 90 ml) was then treated at 20 to 30° C. within 5 to 10 minutes with 13.2 g (0.079 mol) of a solution of hydrochloric acid in isopropanol (21.7%). Upon slow addition of 120 ml heptane crystallization of the product occurred. The resulting suspension was stirred at 40° C. for 2 hours and then cooled to 0 to 5° C. within 2 hours. After one hour at 0 to 5° C. the crystals were filtered, washed in two portions with a pre-cooled mixture of 62 ml heptane and 31 ml isopropanol and dried in vacuo (<30 mbar) at 70° C. for 10 hours to afford 35.5 g (93.5%) of isobutyric acid (2R,3S,4R,5R)-5-(4-amino-2-oxo-2H-pyrimidin-1-yl)-2-azido-3,4-bis-isobutyryloxy-tetrahydro-furan-2-ylmethyl ester hydrochloride with an assay of 99.5% (m/m).

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A process for the preparation of 4'-azido-cytidine (I)

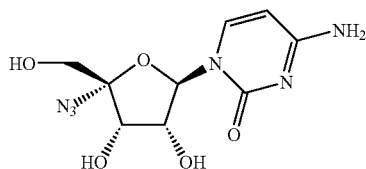

or of a pharmaceutically accepted salt thereof, comprising the steps of:
   a) contacting a 4'-azido-nucleoside of the formula II

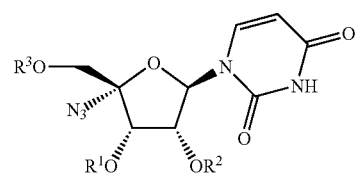

wherein:
   $R^1$ and $R^2$ are independently selected from $COR^4$ and $C(=O)OR^4$ or $R^1$ and $R^2$ together form a —$CH_2$—, —$C(CH_3)_2$—, —CH-phenyl- or —CH(OMe)- a bridge;
   $R^3$ is selected from $COR^4$ and $C(=O)OR^4$ and
   $R^4$ is independently $C_{1-12}$-alkyl, phenyl optionally substituted with 1 to 3 substituents selected from the group consisting of $C_{1-6}$-alkyl, $C_{1-6}$-alkoxy, halogen, nitro or cyano;
   with imidazole, phosphorous oxychloride and triethylamine, optionally in the presence of a first organic solvent, to form an imidazole compound of formula IIIa

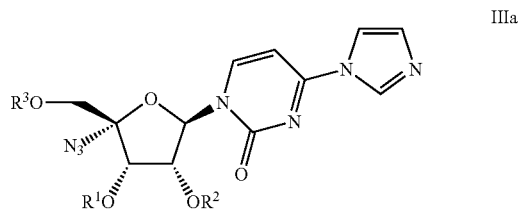

wherein $R^1$, $R^2$ and $R^3$ are as above;
   b) contacting the compound of formula IIIa with aqueous ammonia and a second organic solvent to form an amine of formula IIIb;

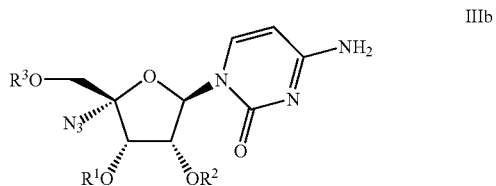

wherein $R^1$, $R^2$ and $R^3$ are as above; and,
   c) deprotecting the amine of formula IIIb to afford 4'-azido-cytidine (I).

2. A process according to claim 1 wherein the imidazole compound of formula IIIa in step
   a) is performed in the presence of a first organic solvent at a temperature of 0° C. to 80° C.

3. A process according to claim 2 wherein said first organic solvent is methylene chloride, tetrahydrofuran or 2-methyl-tetrahydrofuran.

4. A process according to claim 3, wherein the imidazole compound of formula IIIa is directly used for the ammonolysis in step b) without isolation.

5. A process according to claim 4 wherein the ammonolysis in step b) is performed at a temperature of 20° C. to 60° C.

6. A process according to claim 5 wherein the second organic solvent is tetrahydrofuran, 2-methyltetrahydrofuran or methylene chloride.

7. A process of claims 6 wherein the amine of formula IIIb is directly used for the transformation in step c) without isolation.

8. A process according to claim 7 wherein $R^1$, $R^2$ and $R^3$ are independently selected from $COR^4$ and $C(=O)OR^4$ the deprotection in step c) is performed in aqueous ammonia and methanol at a temperature of 20° C. to 60° C.

9. A process according to claim 1 wherein $R^1$ and $R^2$ are taken together form a —$CH_2$—, —$C(CH_3)_2$—, —CH-phenyl- or —CH(OMe)- bridge and $R^3$ is independently selected from $COR^4$ and $C(=O)OR^4$ wherein $R^4$ is as defined above and the deprotection in step c) comprises a first step wherein $R^3$ is cleaved in aqueous ammonia and methanol at a temperature of 20° C. to 60° C. and a second step comprising an acidic treatment to cleave the bridge formed by $R^1$ and $R^2$.

10. A process according to claim 9 wherein the acidic treatment is performed with formic acid.

11. A process according to claim 1 wherein $R^1$ and $R^2$ are benzoyl or $R^1$ and $R^2$ together are —CH(OMe)- and $R^3$ is 3-chlorobenzoyl.

12. A process according to claim 1 for the preparation of a compound according to formula

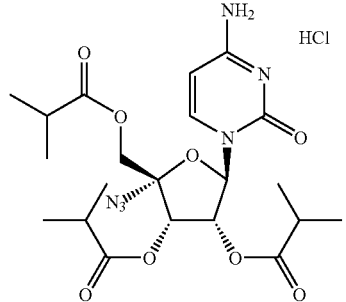

IV which process comprises the additional step of acylating I with isobutyryl chloride in the presence of 4-(dimethylamino)-pyridine and triethylamine in a mixture of water and an organic solvent.

13. A compound of formula IIIa wherein $R^1$ and $R^2$ are independently selected from $COR^4$

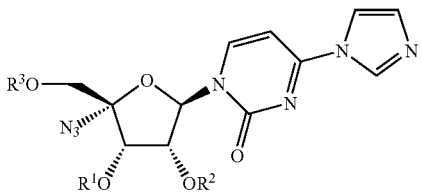

and $C(=O)OR^4$ or $R^1$ and $R^2$ taken together form a $CH_2-$, $C(CH_3)_2-$, CH-phenyl- or —CH(OMe)- bridge;

$R^3$ is selected from $COR^4$ and $C(=O)OR^4$ and $R^4$ is independently $C_{1-12}$-alkyl, phenyl optionally substituted with 1 to 3 substituents selected from the group consisting of $C_{1-6}$-alkyl, $C_{1-6}$-alkoxy, halogen, nitro or cyano.

14. A compound according to claim 12 wherein $R^1$ and $R^2$ are benzoyl or $R^1$ and $R^2$ together are —CH(OMe)- and $R^3$ is 3-chlorobenzoyl.

* * * * *